(12) United States Patent
Yeon et al.

(10) Patent No.: US 10,016,281 B2
(45) Date of Patent: Jul. 10, 2018

(54) SPINAL INTERVERTEBRAL IMPLANT

(71) Applicants: Howard Yeon, Tuxedo Park, NY (US); David Smith, Hoboken, NJ (US)

(72) Inventors: Howard Yeon, Tuxedo Park, NY (US); David Smith, Hoboken, NJ (US)

( * ) Notice: Subject to any disclaimer, the term of this patent is extended or adjusted under 35 U.S.C. 154(b) by 0 days.

(21) Appl. No.: 14/822,387

(22) Filed: Aug. 10, 2015

(65) Prior Publication Data
US 2016/0038300 A1 Feb. 11, 2016

Related U.S. Application Data

(60) Provisional application No. 62/035,020, filed on Aug. 8, 2014.

(51) Int. Cl.
A61F 2/44 (2006.01)
A61F 2/30 (2006.01)

(52) U.S. Cl.
CPC ... A61F 2/4455 (2013.01); *A61F 2002/30112* (2013.01); *A61F 2002/30168* (2013.01)

(58) Field of Classification Search
CPC .................... A61F 2/4455; A61F 2002/30168
See application file for complete search history.

(56) References Cited

U.S. PATENT DOCUMENTS

| | | | |
|---|---|---|---|
| 3,867,728 A | 2/1975 | Stubstad et al. | |
| 4,479,491 A * | 10/1984 | Martin | A61B 17/70 606/246 |
| 5,609,637 A | 3/1997 | Biedermann et al. | |
| 6,143,032 A | 11/2000 | Schafer | |
| 6,245,108 B1 | 6/2001 | Biscup | |
| 6,395,031 B1 | 5/2002 | Foley et al. | |
| 6,648,915 B2 | 11/2003 | Sazy | |
| 6,723,126 B1 | 4/2004 | Berry | |
| 7,094,257 B2 | 8/2006 | Mujwid et al. | |
| 7,806,932 B2 | 10/2010 | Webb et al. | |
| 8,002,833 B2 * | 8/2011 | Fabris Monterumici | A61B 17/025 623/17.11 |
| 8,110,004 B2 | 2/2012 | Valdevit et al. | |
| 8,216,317 B2 * | 7/2012 | Thibodeau | A61F 2/4455 606/279 |
| 8,591,589 B2 | 11/2013 | McCombe et al. | |
| 8,632,595 B2 | 1/2014 | Weiman | |
| 8,900,307 B2 | 12/2014 | Hawkins et al. | |
| 2002/0019637 A1 | 2/2002 | Frey et al. | |
| 2004/0153065 A1 | 8/2004 | Lim | |

(Continued)

FOREIGN PATENT DOCUMENTS

DE 102004024046 A1 * 12/2004 ............. A61B 17/70

*Primary Examiner* — Ellen C Hammond

(57) ABSTRACT

An implant to be surgically positioned between two adjacent vertebrae made of a biocompatible material having two distinct areas of geometry—a front/anterior distracting portion and a second stabilizing back end/posterior portion. The device is inserted into the disc space on its side—in a first position—up until a point and then the device is rotated 90 degrees along a z-axis—into a second position—and then pushed the remainder of the way into the disc space. As viewed from the bottom of the device (in the second position—the position of the implant after rotation, the device is L-shaped, about L-shaped, or an angled dual leg configuration. A base member forms an angle anywhere between 30 to 150 degrees with a connected extended member.

15 Claims, 14 Drawing Sheets

(56) References Cited

U.S. PATENT DOCUMENTS

2006/0217807 A1 9/2006 Peterman et al.
2015/0196400 A1* 7/2015 Dace .................... A61F 2/4455
623/17.16

* cited by examiner

SPINAL INTERVERTEBRAL IMPLANT

CROSS-REFERENCE TO RELATED APPLICATION

This application claims the benefit of U.S. Application Ser. No. 62/035,020 filed on Aug. 8, 2014 which is expressly incorporated herein in its entirety by reference thereto.

FIELD OF THE INVENTION

The invention relates to a novel spinal device intended to be implanted in the interbody (intervertebral) disc space after partial or subtotal surgical removal of the intervertebral disc through a transforaminal approach (TLIF) or posterior lumbar approach (PLIF). More specifically, the invention relates to spinal implant devices configured to distract the vertebral bodies during insertion, the implant device capable of being rotated while positioned within the intervertebral space such that the implant creates stable, lordotic, vertebral body spacing.

BACKGROUND OF THE INVENTION

The human spine is composed of seven cervical, twelve thoracic, five lumbar vertebrae, the sacrum and the coccyx. Vertebrae increase in size starting from the cervical spine through the bottom of the lumbar spine and are generally shaped as oval cylinders with concave upper and lower surfaces/endplates. Mobile segments of the cervical, thoracic and lumbar spine are joined by paired left and right arthrodial joints posteriorly, intervertebral discs anteriorly and circumferential stabilizing ligaments. The spine serves the dual role of providing skeletal support for the trunk, maintaining appropriate skull position and protecting the spinal cord and spinal nerves from trauma or compression.

Appropriate spinal alignment is characterized by balance in the coronal (left-right) and sagittal (anterior-posterior) planes. Among other concepts, balance involves the centering of a plumb line dropped from the neck or skull over the pelvic midline to ensure that excessive soft tissue stresses are not required to achieve or maintain good posture. Radiographic conventions are used to define balance. In the sagittal plane, the C7 vertebra is said to be in balance if a plumb line dropped from the center of the vertebra intersects the superior/posterior corner of the S1 vertebra. In the coronal (side to side) plane, the spine is said to be in balance if a plumb line dropped from the midpoint/spinous process of C7 intersects the midpoint of the S1 vertebra.

Radiographic criteria defining acceptable sagittal balance are sometimes defined at the top of the thoracic and bottom of the lumbar spine, because of variations among individuals in the extent of natural thoracic kyphosis (apex posterior concavity) and lumbar lordosis (apex anterior convexity). There exists significant variation in terms of not only the degree of kyphosis and lordosis but also in the location/level of the transition between kyphosis and lordosis (inflection area). Still, with regard to the lumbar spine, the lowest disc spaces, L3-L4, L4-L5 and L5-S1 contribute to the greatest extent to the aggregate lordosis of the lumbar spine.

Over three decades ago, Francis Denis proposed a three column concept of spine stability. His widely recognized system divides the spine into anterior, middle and posterior columns. The anterior column is comprised of the anterior longitudinal ligament and the anterior half of the vertebral body and intervertebral disc, the middle column comprises the posterior longitudinal ligament and posterior half of the vertebral body and intervertebral disc and the posterior column comprises the transverse processes, pedicles, laminae, facet joints, ligamentum flavum and posterior spinal ligaments including the supraspinous and interspinous ligaments.

As the spine ages, a predictable sequence of degenerative changes occur. Aging brings a loss of hydration of disc cartilage and derangement of the disc's internal architecture that can contribute to a loss of disc height and a variable degree of circumferential bulging. As a result of our uniquely upright posture, the structural curvature of the spine and gravity, the lowest three intervertebral discs are most frequently affected by degenerative changes at the earliest age and most severely as degenerative changes progress.

Loss of disc height and disc bulging with or without concomitant bulging of adjacent fibrous joint capsule tissues and osteophyte (bone spur) formation may result in irritation or impingement of adjacent neural structures. Another common cause of nerve irritation is a disc herniation characterized by displacement of fragmented disc material toward the spinal canal. Nerve root irritation causes radiating "sciatic" leg pain that typically radiates from the lower back to one or both legs. Some further believe that degenerative or damaged intervertebral discs may be the source of severe low back pain in some patients.

Degenerative changes that affect intervertebral discs may also lead to deformities of the spine in either the sagittal or coronal plane. Curvature in the coronal plane is termed a "scoliosis"; loss of balance in the sagittal plane is termed "positive" imbalance if it results in an anterior shift in posture and "negative" imbalance if it results in a posterior shift.

Degenerative loss of disc height leads to a disproportinate shortening of the anterior and middle columns of the spine relative to the posterior column that may retain its length better in the face of aging. Aging influences sagittal balance in the direction of positive imbalance for two principal reasons. First, the lowest lumbar discs are usually the most lordotic in the healthy spine, and those discs are also among those most frequently affected by degenerative loss of height. Also, loss of lordosis in the lower lumbar spine has the greatest effect on neck and head position because those discs are furthest away and have the longest radius of action.

Spine surgeons are becoming increasingly aware that age-related changes in sagittal spinal balance may be a key factor in the development of back pain and decreased quality of life and mobility. Though further research is required in this area, it is possible that spine surgeons historically underestimated the degree of spinal sagittal malalignment by neglecting the effect of changes in the sacropelvic axis that initially compensate for positive sagittal imbalance. As the spine tilts forward out of sagittal balance, the pelvis may tilt backward (retrovert) to maintain posture. This rotation decreases the anatomic range of motion of the hip joint in extension and it moves the base of the spine posterior to the weight bearing axis of the hip joints.

A variety of surgical techniques have been developed to treat degenerative spine conditions. Most relevant to this invention, spinal fusion procedures are intended to immobilize adjacent vertebrae by means of a surgically created osseous bridge. Spinal fusion is performed for patients whose spine is initially unstable or where removal of bone, joints, disc or ligamentous structures to effect required decompression of neural elements would render the spine unstable. Fusion is also necessary after surgical techniques are used to correct spinal deformities to ensure that the spine will durably retain its corrected position.

Surgical correction of spinal alignment or balance is accomplished using a variety of surgical techniques. Among these, spinal osteotomies, often in concert with the use of intervertebral implants, are the most widely performed. Corrective osteotomies involve either shortening of the posterior column only (e.g. Smith-Petersen osteotomy), or shortening of all three columns of the spine (e.g. pedicle subtraction osteotomy). Selection among osteotomy techniques involves an assessment of the degree of deformity, the amount of correction desired and the spinal levels where the osteotomy is planned.

Intervertebral implants have been developed to assist surgeons in achieving the goals of lumbar spine fusion surgery. Interbody implants may be composed of a variety of biocompatible materials with differing moduli of elasticity, and they may be implanted after a variety of surgical approaches including the anterior, lateral and posterior approach to the spine. Relevant to the instant invention, the posterior approach to the disc space has the benefit of not requiring an additional surgical incision and in general does not endanger the lumbar plexus, the intestines nor the great vessels as a lateral or anterior approach would. However, the posterior insertion of intervertebral implants is limited by the degree to which the neural structures can be mobilized and retracted to make room for passage of the implant. Typically, the eponymous "Kambin's Triangle" bounded by the exiting nerve root laterally, the traversing nerve root medially and the superior border of the caudal vertebra is <15 mm in transverse dimension.

The internal trabecular anatomy of the vertebrae has been studied carefully both by histologic analysis and by radiographic measurement. Consistently, it has been shown that trabecular thickness, density and bone strength are higher in the posterior aspect of the vertebral body, especially in the area near the medial border of the base of the pedicle. This pattern may be expected to be particularly characteristic in the lower lumbar vertebrae where the weight-bearing access of the spine falls preferentially in the middle column, and Wolff's law would suggest that bone would be stronger in this region as a biologic reaction to increased weight-bearing stress.

A multitude of intervertebral implants intended for posterior implantation exist. Though various geometries exist including devices that change shape or expand once they have been inserted into the disc space, several challenges remain:

a) Maximum implant size is limited by the medial-lateral and cephalad-caudal dimension of the implant, especially at the upper part of Kambin's Triangle where the exiting nerve root is most medial. Medial mobilization of the traversing nerve root requires additional surgical time and risk. Through less invasive approaches, surgical visualization of medial or lateral neural structures and may be limited.

b) The maximum degree of lordosis of the implant is constrained as the largest side of the implant is the first part inserted into the disc space, and this largest dimension of the implant must accommodate passage through Kambin's triangle. Especially in weakened, osteoporotic bone, forcible insertion of the largest part of the implant may result in partial endplate fracture that propagates forward along the track of insertion (plowing) resulting in an implant that has compromised structural support.

c) As a result of constraints on the maximum achievable degree of lordosis, surgeons have not been able to rely on interbody devices alone to achieve restoration or augmentation of lordosis. Implants inserted from a PLIF or TLIF approach or technique are especially limited in terms of restoration of lordosis because of the geometric constraints discussed above.

d) Devices that are inserted with smaller dimensions and are expanded once they are inserted into the interbody space carry the potential for mechanical failure of the expansion mechanism either during insertion making expansion impossible or resulting in a potentially loose implant that may be difficult to remove once partially expanded in the intervertebral space. Lack of tactile feedback during implant expansion may result in endplate fracture and implant subsidence. The design of expandable implants are generally require the implant to be solid, without a graft window, and the footprint of the graft becomes an area where interosseous fusion cannot take place.

e) To determine the most appropriate implant size, multiple trial implants if increasing size are generally inserted prior to insertion of the final, retained implant. This process is time consuming, involves multiple forcible passes of instruments adjacent to neural structures and with each passage, it increases the likelihood of damage to the endplate.

Accordingly, there is a need for an improved intervertebral implant, intended for implantation through a posterior approach, that addresses these drawbacks.

SUMMARY OF THE INVENTION

Applicants have invented a new spinal implant device that overcomes these and other shortcomings. While the invention will be described in connection with certain embodiments, it will be understood that the invention is not limited to those embodiments. To the contrary, the invention includes all alternatives, modifications and equivalents as may be included within the spirit and scope of the present invention.

The invention is an intervertebral implant intended to be surgically positioned between two adjacent spinal vertebrae either through a conventional open or minimally invasive approach. The implant is made of a biocompatible material and has two distinct areas of design geometry—the front/anterior distracting portion and a second stabilizing back end/posterior portion. The implant may be of singular construction, or it may be comprised of multiple component parts that are inserted into the surgical site independently and mechanically joined once they are partially or completely implanted.

The implant according to the invention is preferably a single unitary structure. The implant according to the invention has a unique configuration that facilitates posterior installation using a larger implant than currently available. The implant could be described as L-shaped, about L-shaped, and/or with a dual member configuration, depending on the specific embodiment of the invention.

The implant is configured such that it is initially inserted into the disc space on its side—in a first position—up until a point (at least about halfway up the longitudinal length of the device) and then the device is rotated 90 degrees along a z-axis—into a second position—and then pushed the remainder of the way into the disc space such that the device is completely within the disc space. As viewed from the bottom of the device in the second position, the position of the implant after it is rotated within the intervertebral disc space, the device is L-shaped, about L-shaped, or an angled dual leg configuration comprising an extended member and a base member connected to the extended member. In the L-shaped configuration, the base member forms a 90 degree angle with the extended member. In the about L-shaped configuration, the base member forms an angle anywhere between about 80 to 100 degrees with the extended member, and in the angled dual leg configuration the base member forms an angle anywhere between 30 to 150 degrees with the extended member.

The interbody spinal implant according to the invention is now described when in a second position, the position it is intended to reside within the intervertebral space. The device comprises an extended member having a front and a back with a base member connected at the back of the extended member. The base member forms an angle, a, with the extended member. The device has a front end, a back end, a top, a bottom, a left side, a right side, a height in the front end between said top and said bottom, a height in the back end between said top and said bottom, a thickness in the front end between the left side and the right side, a thickness in the back end between the left side and the right side, and a longitudinal length from the front end to the back end. The front end is configured about straight between the top and the bottom of the implant. The front end is rounded between the left side and the right side to create a thin edge on the front end. The thickness of the implant between the left side and the right side increases along the extended member from the front end towards the back end of the implant, that is along its longitudinal axis, up to the base member. The top and the bottom of the implant are each curved in a generally convex shape between the front end and the back end such that the height of the front end of the implant (at the thin "blade-like" front edge) is greater than the height of the back end of the implant.

While the invention includes implants of varying dimensions, in each embodiment of the invention the thickness near the front end, not including the rounded portion of the front, is less than one half of the height of the front end of the implant. Preferably the thickness near the front end, not including the rounded front, is less than about one third of the height of the front end of the implant and most preferably, less than about one fourth the height.

The base member is connected to the back of the extended member. The base member extends out at an angle, α, away from the extended member a distance of about two times the thickness at the front end of the implant (not including the rounded front).

In each embodiment, the narrowly curved (blade-like) front of the device (when in the first position) facilitates insertion of the device into the disc space (along a z-axis through the longitudinal length of the device) without damaging the endplates of the vertebrae. The thickness of the device between its sides increases in a wedge-like manner. If the disc space is shorter in height than the thickness of the device, the wedge like configuration helps distract the vertebral bodies as it is pushed in. The device is pushed into the disc space along a Z-axis until at least a portion of the device is within the disc space, preferably at least one half of the device along its longitudinal length, or until the base member is close to or makes contact with the side of the vertebral body. The device is then rotated 90 degrees along a Z-axis further distracting the vertebral bodies, until the top and bottom of the device are in contact with the endplates of the respective vertebral bodies. In this second position, the base member now fits between the vertebral bodies. The implant is then pushed further into the disc space until the back end of the implant is within the disc space.

The generally convex upper and lower surfaces of the device rest within the generally concave endplates of the vertebral bodies. The base member acts like a stabilizing leg for the device within the disc space keeping the device from falling onto one of its sides.

Depending upon the location (e.g., left or right of the spinal column) and the angle for installation (e.g., posterior or posterior but angled a little laterally) the implant according to the invention can be installed either with the left side of the device facing up (superior) or the right side facing up (superior). In other words, the base member may be positioned downward or it may be extending upward before the rotation. And the direction of rotation could be either clockwise or counterclockwise. Accordingly, as viewed from the top of the spine, the implant according to the invention could be installed with the base member extending to the left or to the right of the extended member.

The invention includes embodiments with an extended member having a generally flat left side surface and/or a generally flat right side surface (from the front end until the base member) as well as embodiments with an extended member having a curved left side surface and/or a curved right side surface.

BRIEF DESCRIPTION OF THE DRAWINGS

The accompanying drawings, which are incorporated in and constitute a part of this specification, illustrate embodiments of the invention and, together with the general description of the invention given above and the detailed description of an embodiment given below, serve to explain the principles of the present invention. Similar components of the devices are similarly numbered for simplicity.

FIG. 1 shows a perspective view from a bottom right side of the device.

FIG. 2 is a rear perspective view of the device also from the right side.

FIG. 3 is a right side view of the device showing a higher front end than back end, a curved top and bottom to match the generally concave shape of the vertebral body endplates, and a curved front edge along the front. FIG. 3 shows the desired position of the device when installed in the disc space. The angle of lordosis (β) results from the difference in heights between the front and the back of the device on top and on bottom.

FIG. 4 is a bottom view of the device shown in FIG. 3. The rounded front of the device is shown in FIG. 3. The embodiment in FIG. 3 shows a wedge-like shape for the extending member (the portion from the front of the device up until to the base member which extends upward in FIG. 4) increasing in thickness between the left side and the right side of the device along the length from front to back. Both the left side and the right side of the extending member are generally flat surfaces with rounded edges between them forming a part of the top and a part of the bottom of the device. FIG. 4 shows the about L-shaped configuration with a 105 degree angle (α) between the extending member and the base member.

FIG. 5 is a top view of the device shown in FIG. 3.
FIG. 6 is a front view of the device shown in FIG. 3.
FIG. 7 is a rear view of the device shown in FIG. 3.

FIG. 8 shows a rear perspective view from a bottom right side of the device.

FIG. 9 is a front perspective view of the device also from the right side.

FIG. 10 is a right side view of the device showing a higher front end than back end, a curved top and bottom to match the generally concave shape of the vertebral body endplates, and a curved front edge along the front. FIG. 10 shows the desired position of the device when installed in the disc space. The angle of lordosis (3) results from the difference in heights between the front and the back of the device on top and on bottom.

FIG. 11 is a bottom view of the device shown in FIG. 10. The rounded front of the device is shown in FIG. 11. The embodiment in FIG. 11 shows a wedge-like shape for the extending member (the portion from the front of the device up until to the base member which extends upward in FIG. 11) increasing in thickness between the left side and the right side of the device along the length from front to back. Both the left side and the right side of the extending member are generally flat with rounded edges between them forming a part of the top and a part of the bottom of the device. FIG. 11 shows the angled configuration with a 45 degree angle (α) between the extending member and the base member.

FIG. 12 is a top view of the device shown in FIG. 10.

FIG. 13 is a front view of the device shown in FIG. 10.

FIG. 14 is a rear view of the device shown in FIG. 10.

FIG. 15 shows a rear perspective view from a bottom right side of the device.

FIG. 16 is a front perspective view of the device also from the right side.

FIG. 17 is a right side view of the device showing a higher front end than back end, a curved top and bottom to match the generally concave shape of the vertebral body endplates, and a curved front edge along the front. FIG. 17 shows the desired position of the device when installed in the disc space. The angle of lordosis (3) results from the difference in heights between the front and the back of the device on top and on bottom.

FIG. 18 is a bottom view of the device shown in FIG. 17. The rounded front of the device is shown in FIG. 18. The embodiment in FIG. 18 shows a wedge-like shape for the extending member (the portion from the front of the device up until to the base member which extends upward in FIG. 18) increasing in thickness between the left side and the right side of the device along the length from front to back. Both the left side and the right side of the extending member are generally flat surfaces with rounded edges between them forming a part of the top and a part of the bottom of the device. FIG. 18 shows the L-shaped configuration with a 90 degree angle (α) between the extending member and the base member.

FIG. 19 is a top view of the device shown in FIG. 17.

FIG. 20 is a front view of the device shown in FIG. 17.

FIG. 21 is a rear view of the device shown in FIG. 17.

FIGS. 25 and 26, the bottom and top views, more clearly show the curvature.

FIG. 29 shows a perspective view from a bottom right side of the device.

FIG. 30 is a rear perspective view of the device also from the right side.

FIG. 31 is a right side view of the device showing a higher front end than back end and a curved front edge along the front. FIG. 31 shows the desired position of the device when installed in the disc space. The angle of lordosis (0) results from the difference in heights between the front and the back of the device on top and on bottom.

FIG. 32 is a bottom view of the device shown in FIG. 31. The rounded front of the device is shown in FIG. 32. The embodiment in FIG. 32 shows a wedge-like shape for the extending member (the portion from the front of the device up until to the base member which extends upward in FIG. 32) increasing in thickness between the left side and the right side of the device along the length from front to back. Both the left side and the right side of the extending member are flat surfaces. FIG. 32 shows the L-shaped configuration with a 90 degree angle (α) between the extending member and the base member.

FIG. 33 is a top view of the device shown in FIG. 31.

FIG. 34 is a front view of the device shown in FIG. 31.

FIG. 35 is a rear view of the device shown in FIG. 31.

FIGS. 37 and 38 show how the implant, in a first position on its side (shown with the right side upwards toward the head but it could be alternatively be installed with the right side facing down) is inserted into the disc space. The sides of the device are used to distract the vertebral bodies.

FIGS. 39 and 40 show how the implant reaches a point where the base member is close to or makes contact with the side of the vertebral body preventing the implant from further insertion in the first position. The rotation of the implant along the Z-axis is also shown in FIGS. 39 and 40 it being understood that the device could be rotated either clockwise or counterclockwise depending on the surgical approach used and the position of the device in the disc space.

FIG. 41 shows the rotated device in a second position with the intervertebral discs distracted the full height of the front of the implant.

FIG. 42 shows the implant inserted further into the disc space with the implant secure and stable between the endplates, completely within the disc space, creating lordosis for the spine.

DETAILED DESCRIPTION OF THE INVENTION

Figure 1:
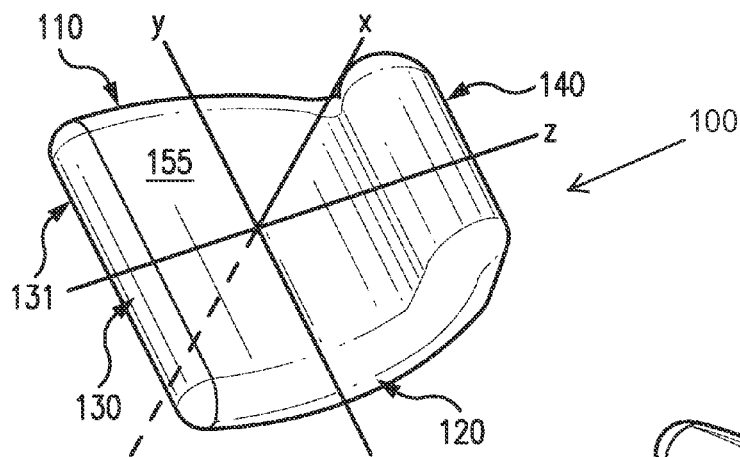
FIGS. 1-7 show one example embodiment of the implant according to the invention in an about L-shaped configuration with a base member at an about 105 degree angle with the extended member.
Figure 2:
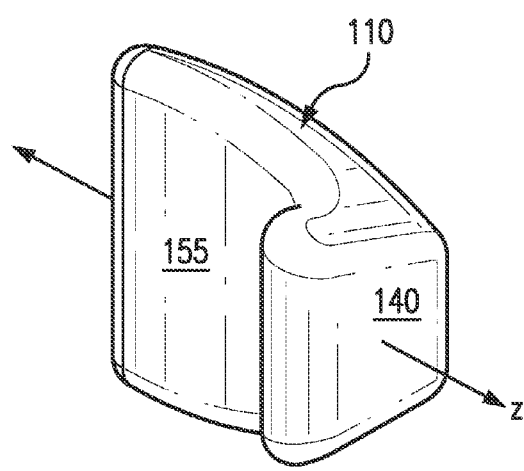

The accompanying drawings, which are incorporated in and constitute a part of this specification, illustrate embodiments of the invention and, together with the general description of the invention given above and the detailed description of an embodiment given below, serve to explain the principles of the present invention. Similar components of the devices are similarly numbered for simplicity.

FIGS. 1-7 show one example embodiment of the angled implant 100 according to the invention in an about L-shaped configuration with a base member 195 forming an about 105 degree angle with an extended member 190. As seen in FIGS. 1-7, implant 100 is in a vertical position when top 110 faces upwards and bottom 120 faces downwards. When viewed from a front view (FIG. 6) implant 100 has base member 195 protruding on the right side 155 of the device 100 in the back end of the device. Device 100 includes front 130, back 140, bottom 120, top 110, right side 155, and left side 165. Axes XYZ are shown in the Figures to assist with descriptions of the various embodiments.

Figure 4:
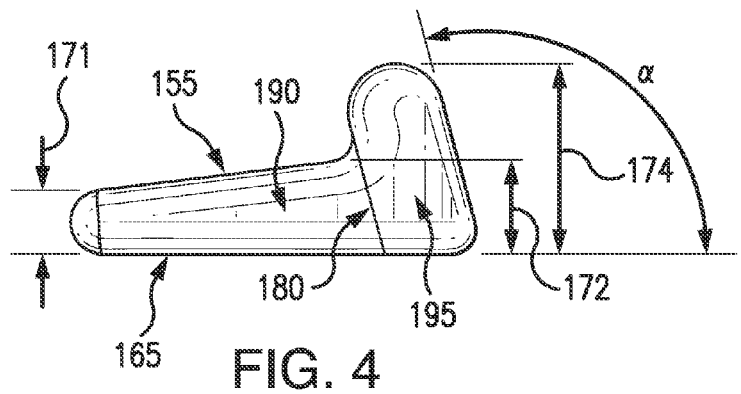
Figure 5:
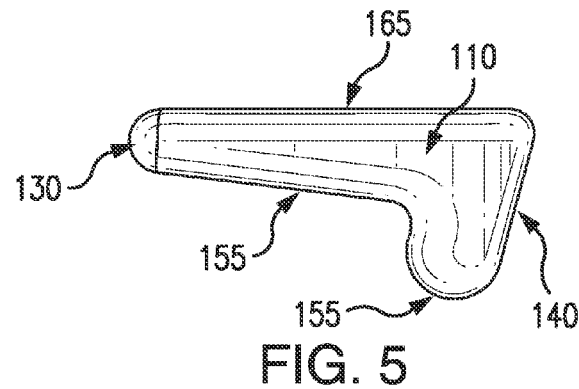
Figure 6:
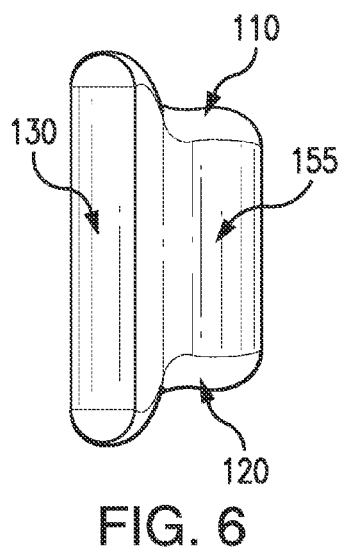
Figure 7:
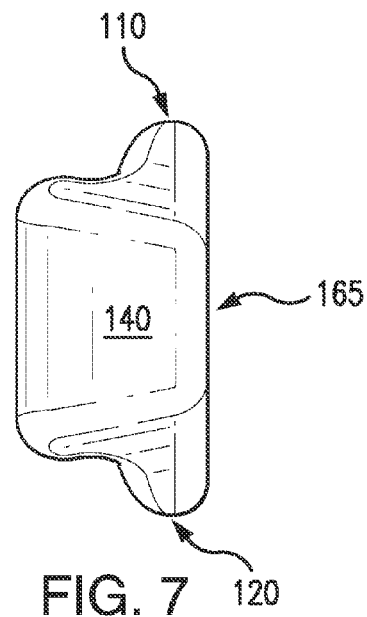
Figure 8:
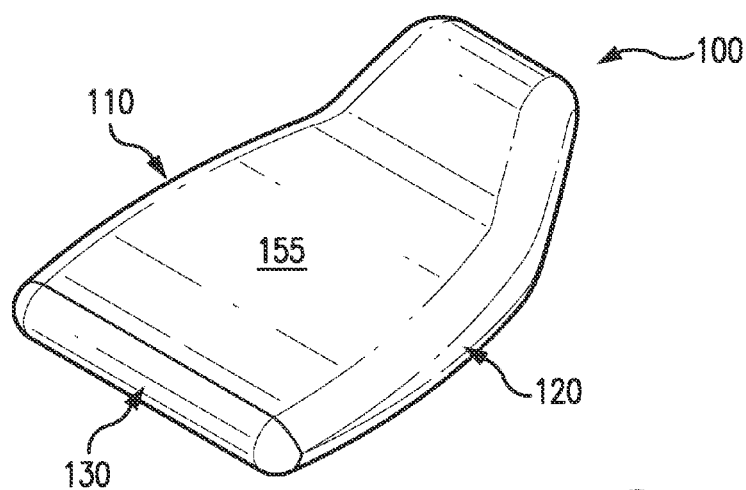
FIGS. 8-14 show another example embodiment of the implant according to the invention in an angled configuration with a base member at an about 45 degree angle with the extended member.
Figure 9:
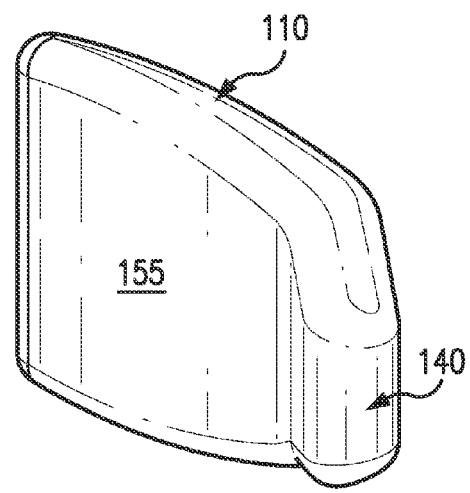
Figure 10:
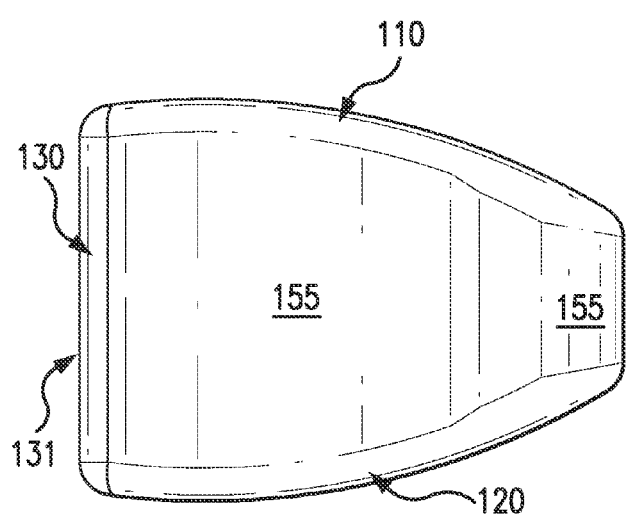
Figure 11:
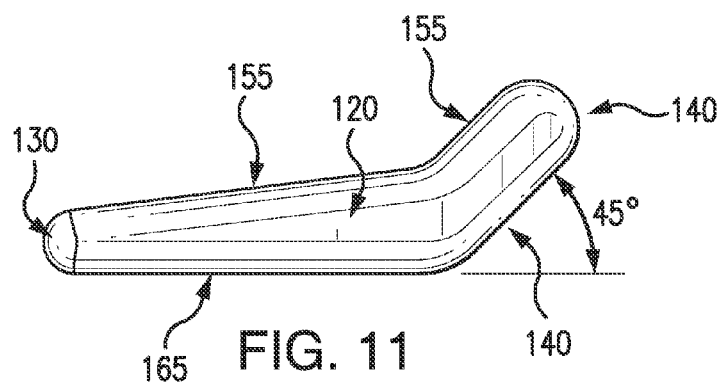
Figure 12:
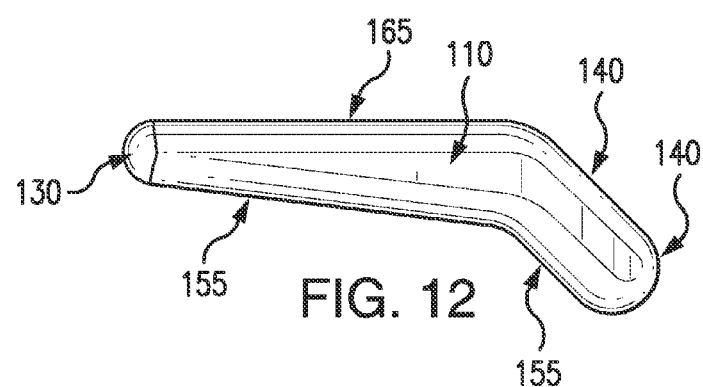
Figure 13:
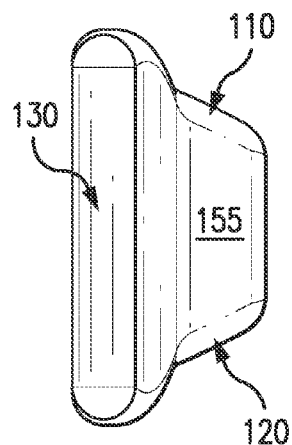
Figure 14:
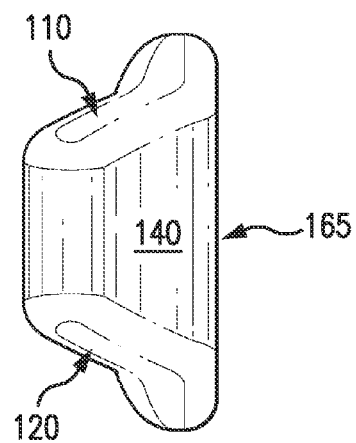
Figure 15:
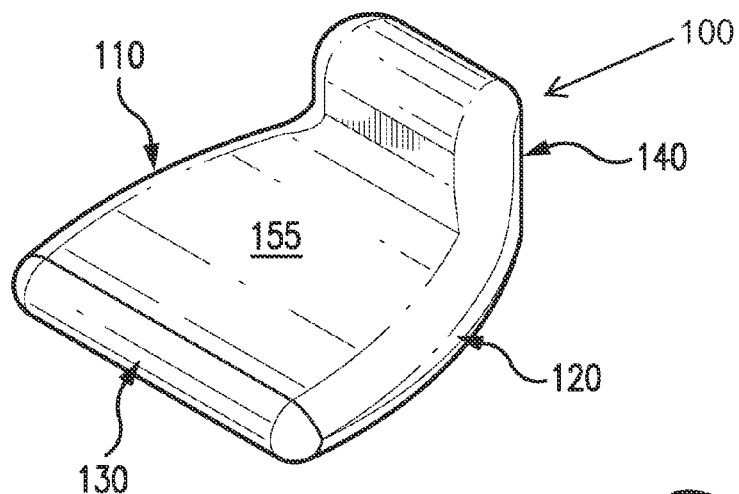
FIGS. 15-21 show yet another example embodiment of the implant according to the invention in an L-shaped configuration with a base member at a 90 degree angle with the extended member.
Figure 16:
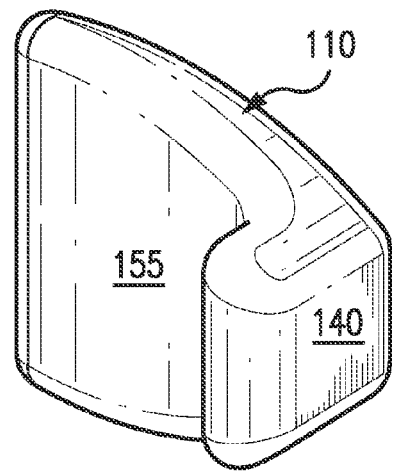
Figure 17:
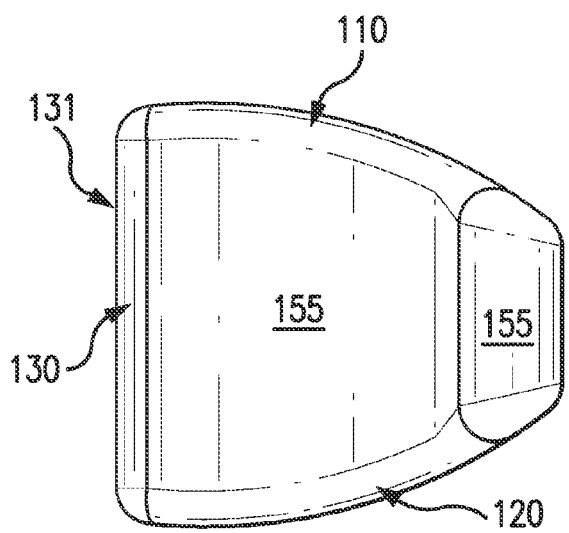
Figure 18:
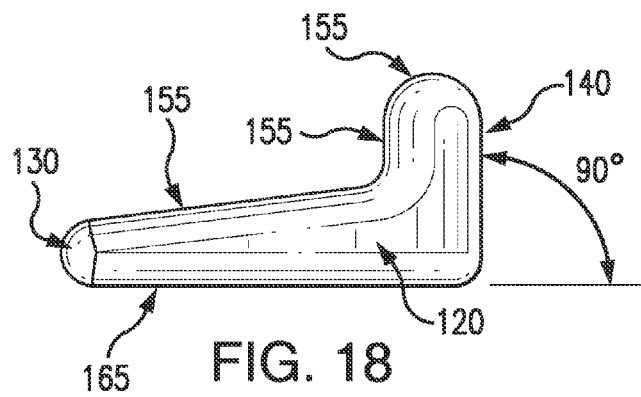
Figure 19:
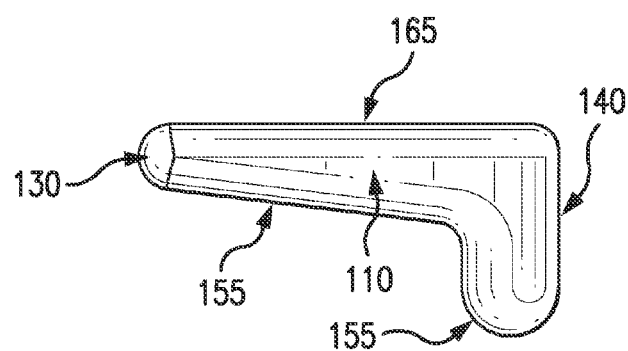
Figure 20:
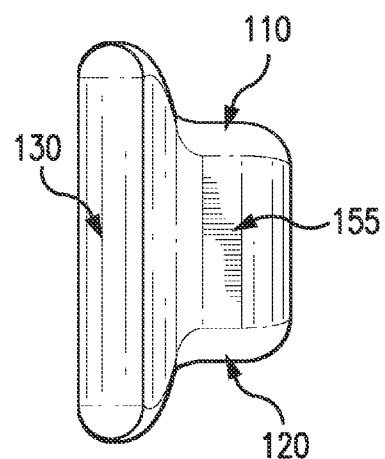
Figure 21:
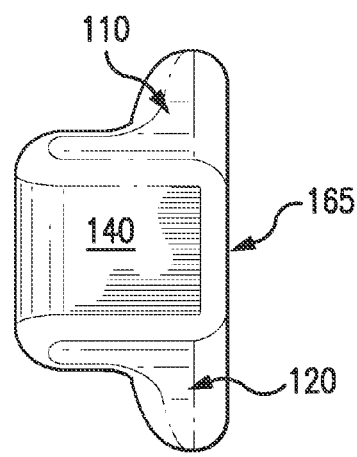
Figure 22:
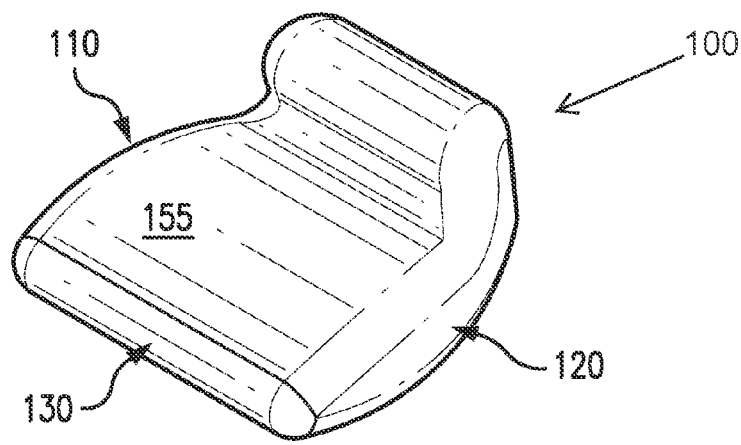
FIGS. 22-28 show yet another example embodiment of the implant according to the invention in an about L-shaped configuration similar to the embodiment shown in FIGS. 1-7 except that the left and right sides of the extended member are curved in a convex configuration.
Figure 23:
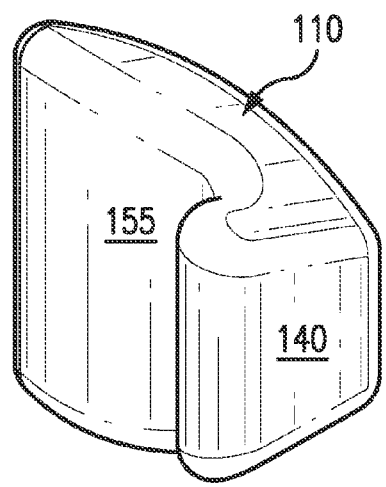
Figure 24:
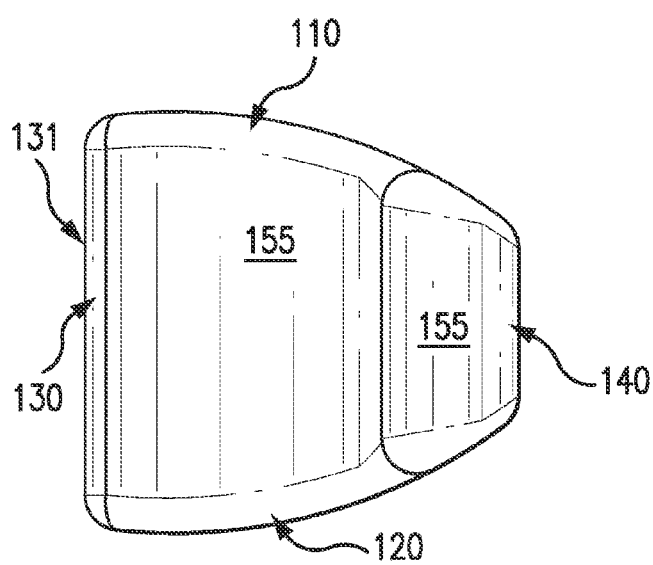
Figure 25:
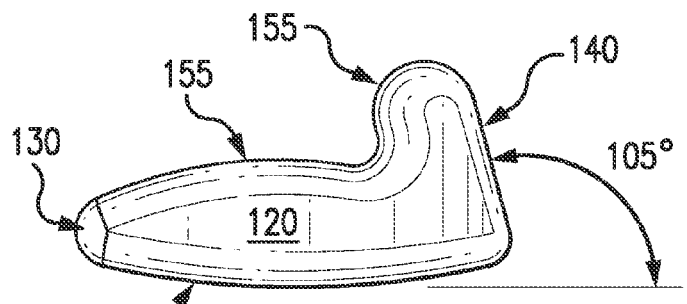
Figure 26:
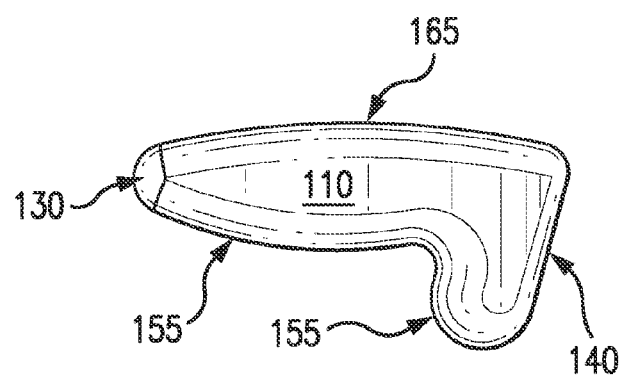
Figure 27:
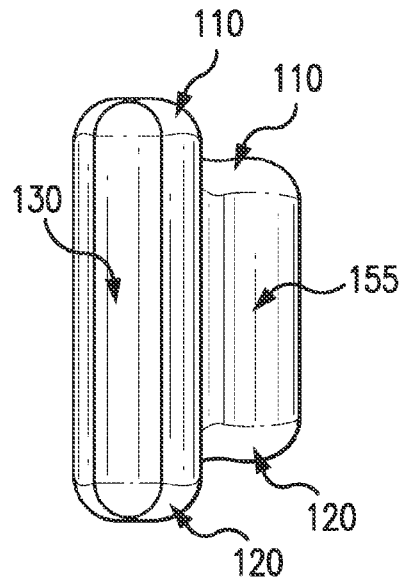
Figure 28:
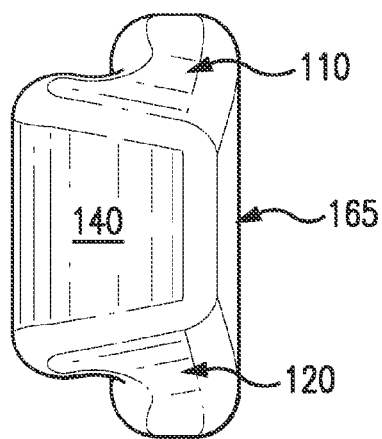
Figure 29:
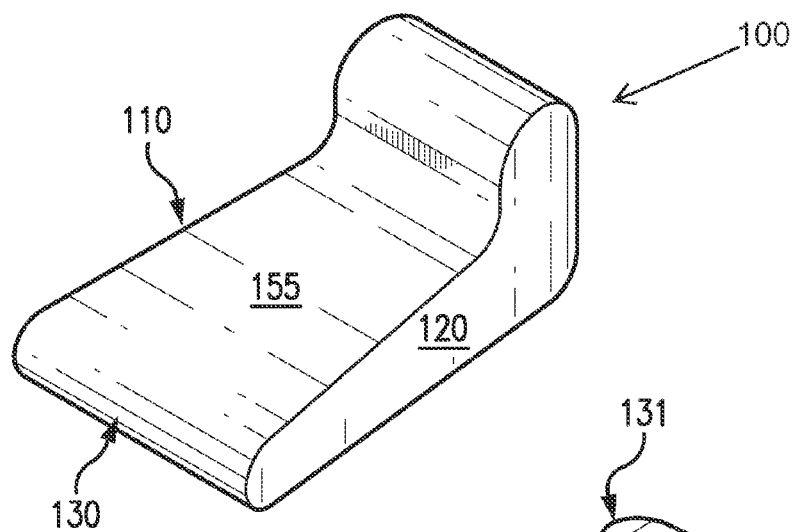
FIGS. 29-35 show yet another example embodiment of the implant according to the invention in an L-shaped configuration with a base member at a 90 degree angle with the extended member. The configuration in FIGS. 29-35 show a flat top surface and a flat bottom surface.
Figure 30:
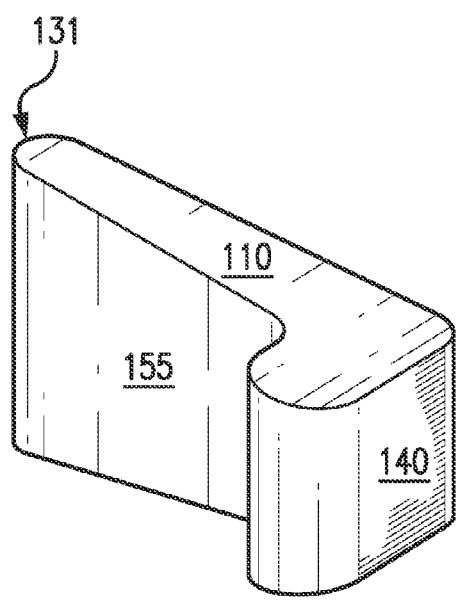
Figure 31:
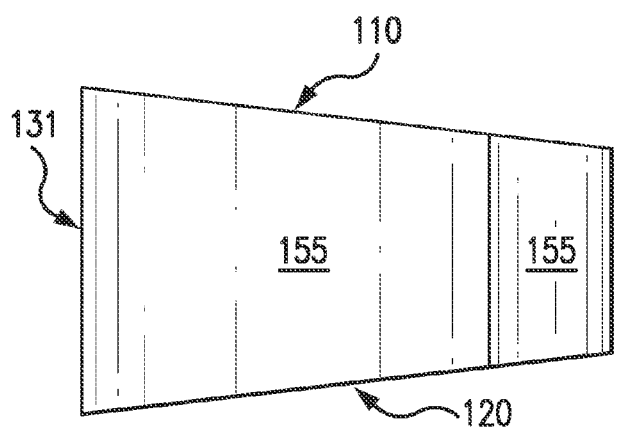
Figure 32:
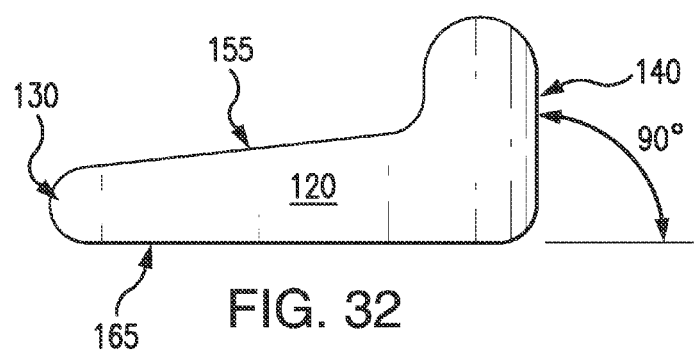
Figure 33:
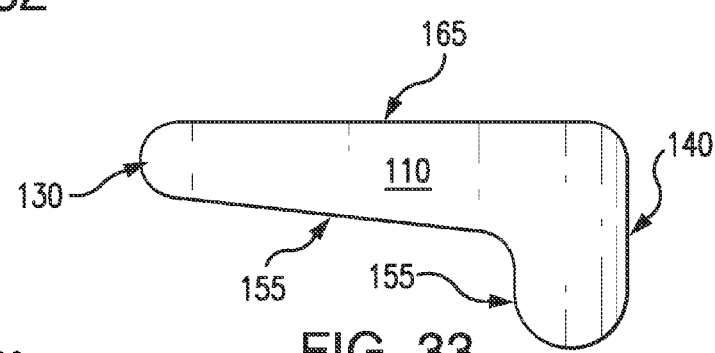
Figure 34:
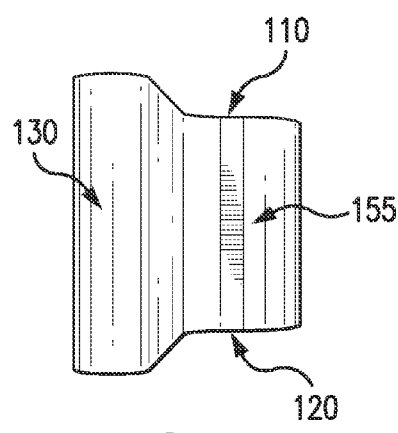
Figure 35:
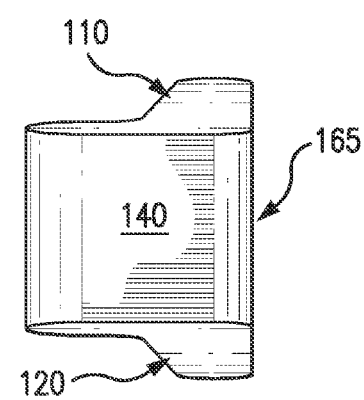

Extended member 190 has an elongated wedge-like shape with a rounded front 130. The front 130 of the device 100 functions much like a wedge with a narrow front in that when the device is turned on its side (either side), a first position, and is pushed between the vertebral bodies into the disc space, the device slips between the vertebrae and pushes them apart. The front 130 of the device 100, when in a first position, is like a blade without a sharp edge. The front 130 fits between the endplates into the disc space, with some force if needed, until the front 130 is in the disc space between the endplates. In one example device, the thickness of the front 130 of the device 100 between the right side 155 and the left side 165 after the rounding, designated 171 in FIG. 4, is approximately 4 millimeters in height, it being understood that other sizes are possible and included in the scope of the invention, including anywhere between 2 to 6 mm. The thickness of the device 100 increases along the extended member 190 along the longitudinal length of the device (along the Z-axis) with a generally flat right side surface 155 and generally flat left side surface 165 as seen in FIGS. 4 and 5. The increase in thickness forms a wedge-like device which can be used to distract the vertebral bodies during insertion with minimal (to no) damage to the endplates. In one example device, the thickness 172 of the extended member 190 between the right side 155 and the left side 165 increases to approximately 6 millimeters where the extended member 190 joins/meets the base member 195, designated 180 in FIG. 4, it being understood that other sizes are possible and included in the scope of the invention, including anywhere between 4 to 10 mm creating angles for the increase in thickness anywhere between 5 to 30 degrees.

In the embodiments shown in FIGS. 1-7, 8-14, 15-21, and 29-35, the left side 165 and the right side 155 of the device 100 are configured as generally flat planar surfaces whereas in the embodiment shown in FIGS. 22-28, left side 165 and right side 155 are shown as curved surfaces (shown as convex but they can also be concave). The invention includes embodiments with different variations of the generally flat and curved side surfaces including, without limitation, a device with a generally flat left side 165 and a curved right side 155 (convex or concave) and vice versa.

The front edge 131 of the device is preferably straight from top 110 to bottom 120 as shown in the embodiments shown in the Figures it being understood that curved and irregular configurations are possible and included in the scope of the invention.

The front 130 of the device 100 is configured with a significantly greater height than thickness in the front 130. Preferably, the height of the front 130 of the device is at least three times greater than the thickness. More preferably, the height 173 of the front 130 of the device is about six times greater than the thickness. In one example device, the height 173 of the front of the device between the top 110 and the bottom 120 is approximately 25 millimeters, designated 173 in FIG. 3, it being understood that other sizes are possible and included in the scope of the invention, including heights anywhere between 12 to 30 mm. The significantly larger height to thickness configuration for the front of the device creates a thin blade-like front edge 131. The device 100 will be manufactured in a wide variety of sizes of varying heights as the size of the disc space varies from one vertebrae to another and from one individual to another.

In the embodiments shown in FIGS. 1-7, 8-14, 15-21, and 22-28, the top 110 and the bottom 120 of the device 100 are rounded between the right side 155 and the left side 165, including the parts on the extended member 190 as well as the base member 195. The rounded surface helps seat the device between the endplates which are generally concave shaped. In the embodiment shown in FIGS. 29-35, the top 110 and bottom 120 are shown as flat surfaces. The invention includes embodiments with different variations of the generally flat and rounded surfaces on top and bottom, including, without limitation, a device with a flat top 110 and a rounded bottom 120, and vice versa.

A base member 195 is connected to the extended member 190 to form an angled implant device. It is preferred that the entire device be made as a single unitary structure although it could be made in two or more component parts. The base member 195 is joined to the extended member 190 at the back end of the extended member (furthest away from the front 130). The thickness of the base member is greater than the thickness of the extended member 190 creating a bump/protrusion on one side of the device 100. In the views for the embodiments shown in the Figures, the bump/protrusion is shown on the right side 155 of the device 100. Preferably, the thickness of the base member 195 is at least 1.5 times greater than the thickness 172 of the extended member 190 in the device. More preferably, the thickness of the base member 195 is at least 2 times greater than the thickness 172 of the extended member 190 in the device and could be 4 to 5 times or more greater than the thickness 172 of the extended member 190. In one example device, the thickness 172 of the extended member is approximately 6 millimeters and the thickness of the base member, designated 174 in FIG. 4, is 12 millimeters, it being understood that other sizes are possible and included in the scope of the invention, including thicknesses for the base member anywhere between 10 to 20 millimeters. The thicker base member 195 provides two functions to the implant device 100: 1) it provides a stop during insertion into the disc space when it contacts the end plate signifying the implant is ready for rotation along a (Z-axis), and 2) it provides stability for the device and the vertebrae when the device is located completely within the disc space—the base member acts like a level arm preventing the implant from toppling over.

The back 140 of the device 100 is the back end of the base member 195. As seen in FIG. 4, a bottom view, the device has an about L-shaped configuration with a 105 degree angle, a, between the generally flat left side 165 and the generally flat back 140. The present invention is not limited to any single angled configuration. Rather, the present invention includes a wide variety of configurations with alternatively sized angle α, including, angles anywhere between 30 degrees to 150 degrees as shown in the other embodiments in the Figures. In the embodiments shown in FIGS. 1-7 and FIGS. 22-28, angle α is 105 degrees. In the embodiment shown in FIGS. 8-14, α is 45 degrees. In the embodiments shown in FIGS. 15-21 and FIGS. 29-35, α is 90 degrees. Different α angles allow for different positioning of the device 100 within the disc space without any part of the device outside the outer circumferences of the endplates. Different α angles for the base member 195 relative to the extended member also allow for different installation angles such as, for example, a trans-lateral approach.

The right side 155 of the base member 195 is rounded between the front most portion and the back most portion similar to the front edge 131 of the device 100.

Figure 3:
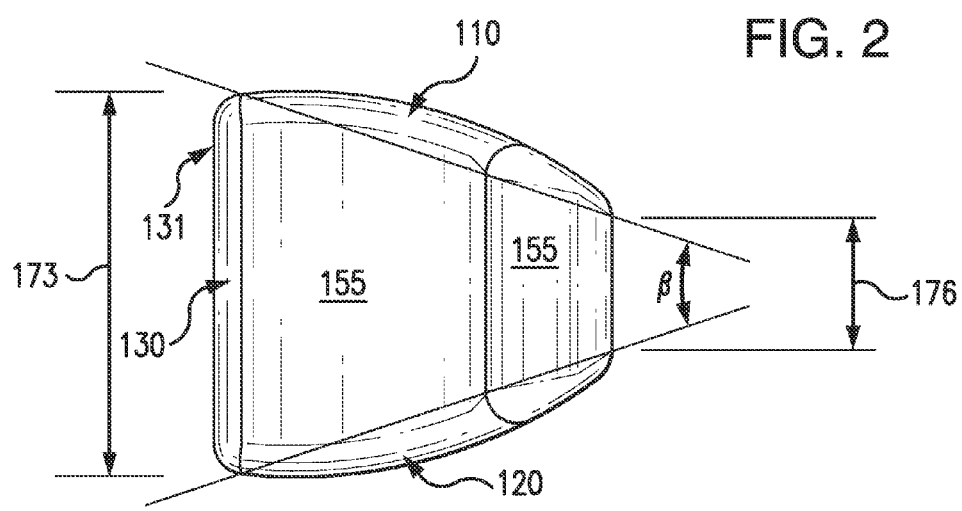

The height of the back 140 of the base member 195, designated 176, is less than the height 173 of the front 130 of the device 100 to create lordosis when the implant is installed. Preferably, the height 176 of the back 140 of the device 100 is configured to create the desired angle of lordosis for the spine which could be anywhere between 0 and 30 degrees. As shown in FIG. 3, the angle of lordosis (β) for the implant device 100 results from the difference in heights between the front and the back of the device on top and on bottom. Existing implant devices create a maximum of about 15 degrees of lordosis whereas the device according to the present invention can create angles up to and greater than 30 degrees. In one example device, the height 173 of the front of the device between the top 110 and the bottom 120 is approximately 20 millimeters and the height 176 of the back of the device is approximately 9 millimeters, with a device length of 26 millimeters, thus creating an about 20 degree angle β. It is understood that other sizes and angles are possible and included in the scope of the invention, including heights for the back anywhere between 6 to 20 millimeters.

In the embodiments shown in FIGS. 1-7, 8-14, 15-21, and 22-28, the top 110 and the bottom 120 of the device 100 are configured generally convex in shape along the longitudinal length (along the Z-axis) of the device 100. Alternatively, as shown in FIGS. 29-35, the top 110 and bottom 120 of the device 100 are configured generally flat and straight from front to back along the longitudinal length (along the Z-axis) of the device 100. The invention includes embodiments with different variations of the generally convex and generally flat and straight surfaces on top and bottom, including, without limitation, a device with a generally flat and straight top 110 with a convex bottom 120, and vice versa.

Figure 36:
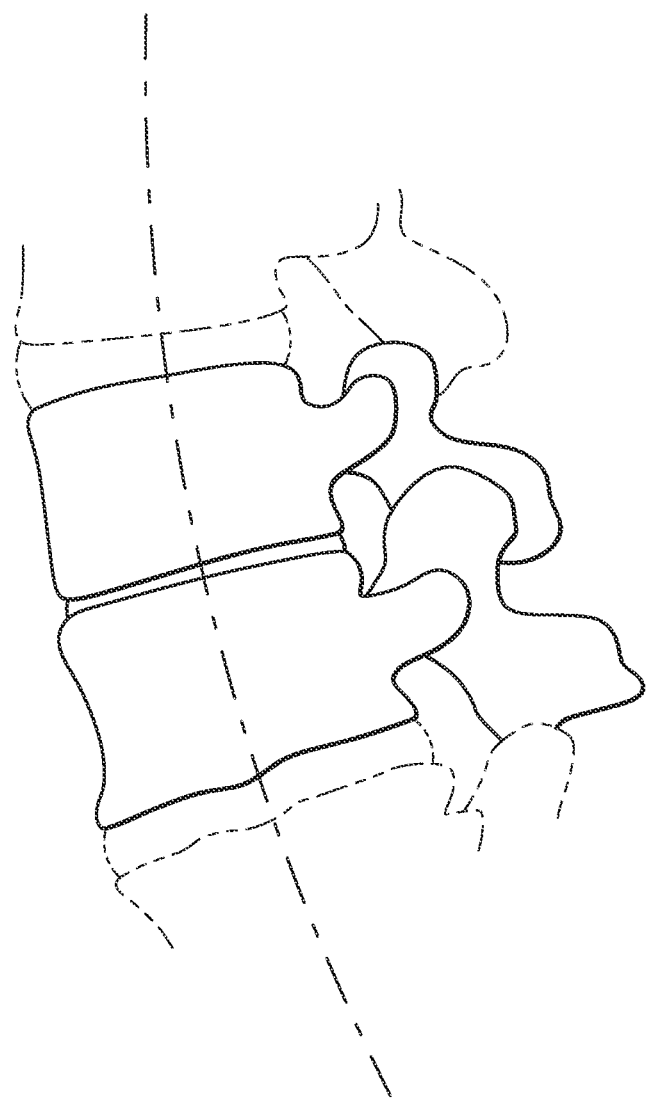
FIG. 36 is a side view of a portion of a spine in the lumbar region showing two vertebral bodies and a disc between them.
Figure 37:
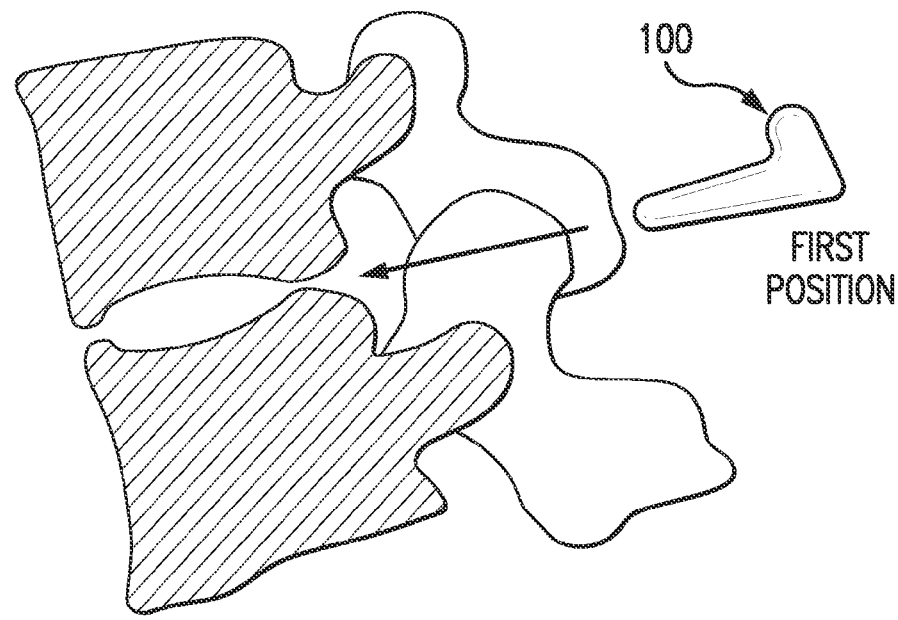
FIGS. 37-42 illustrate how one implant according to the invention is installed in the spine posteriorly.
Figure 38:
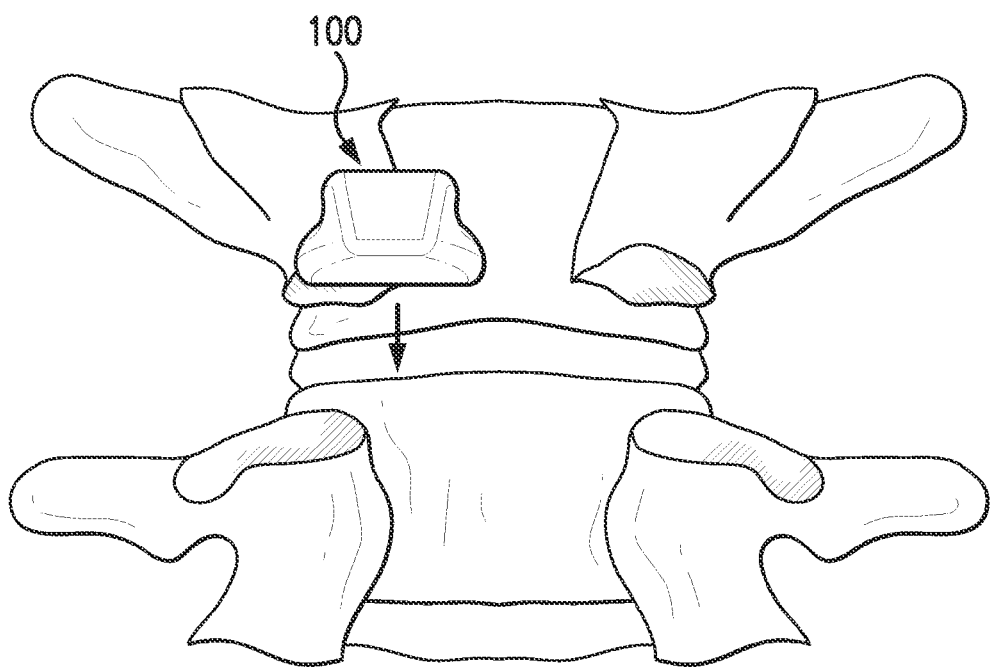
Figure 39:
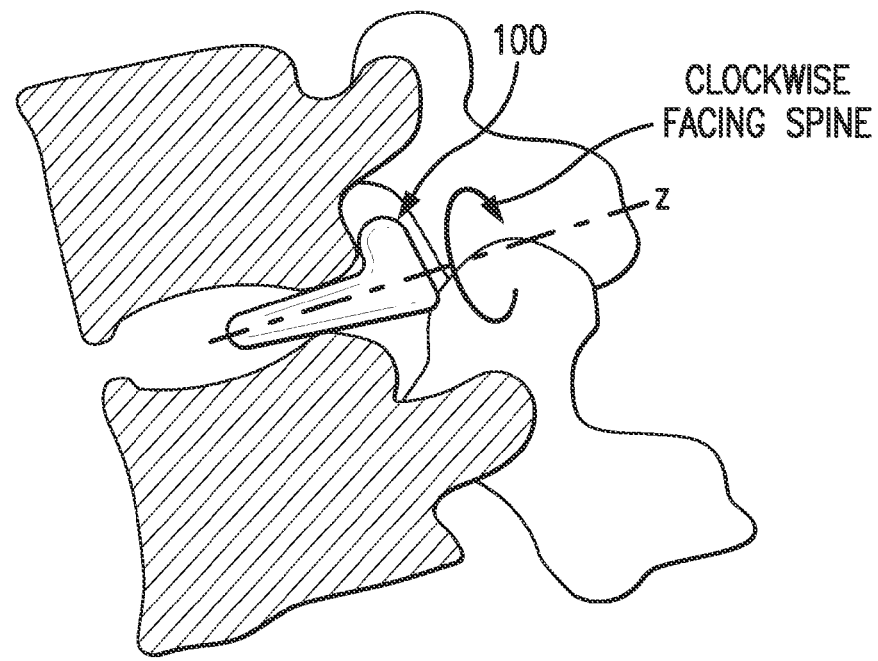
Figure 40:
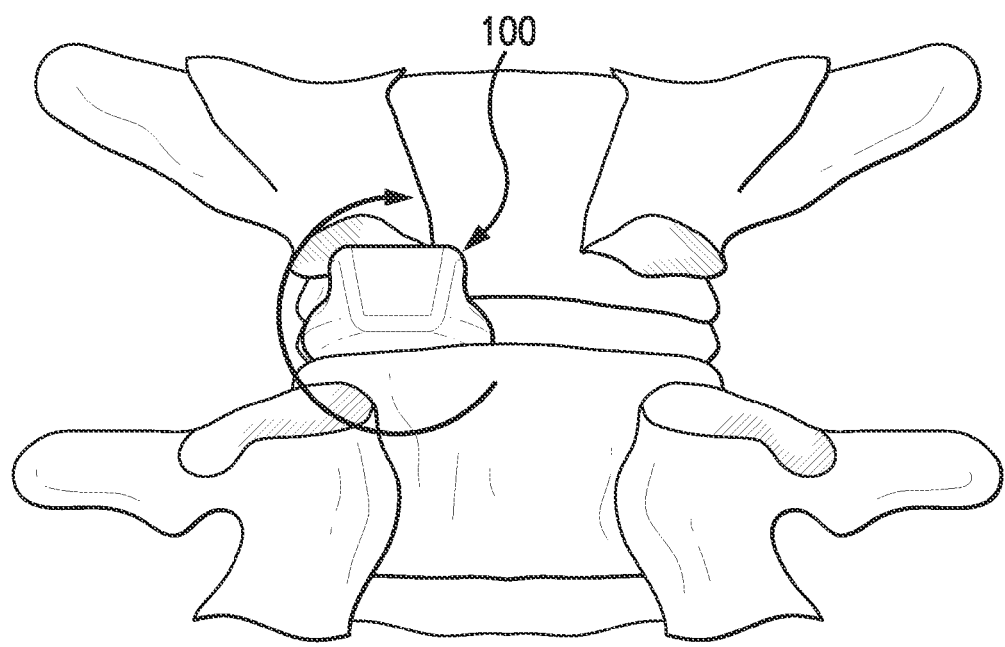
Figure 41:
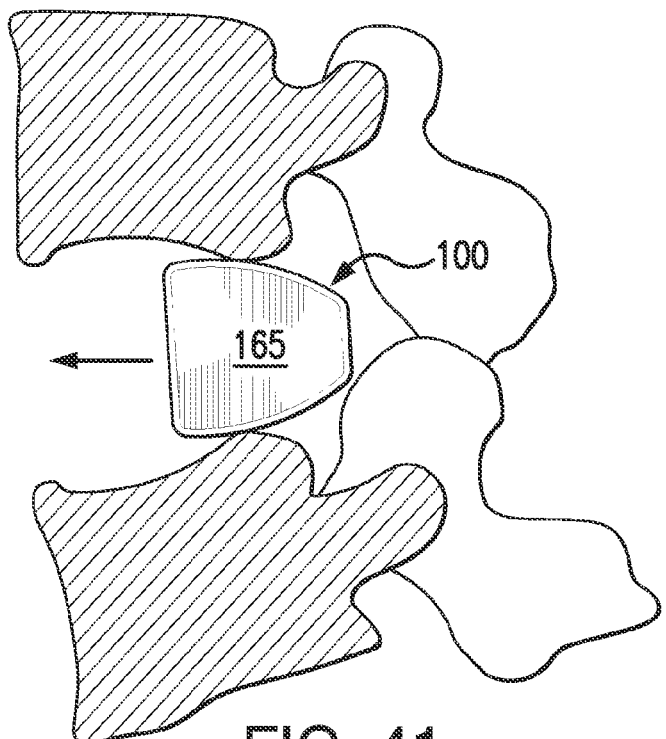
Figure 42:
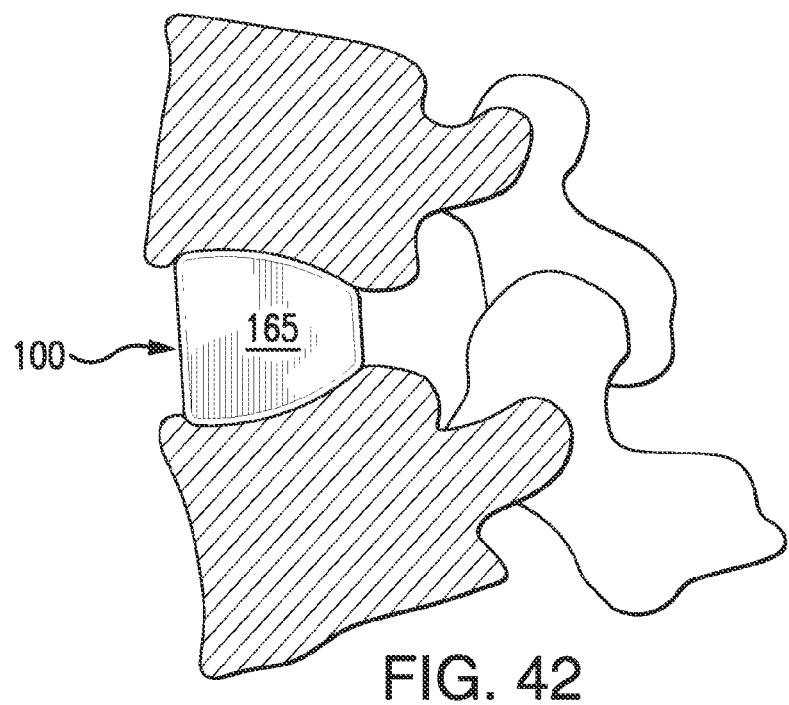

The method of installation of the device is described and shown using FIGS. 36-42. FIG. 36 shows a side view of a part of a spine in the lumbar region showing two full vertebrae. FIG. 37 is a cross section view of FIG. 36 showing the device 100 in a first position on a side with the right side 155 superior. The device 100 is inserted into the disc space posteriorly as shown in FIGS. 37 and 38 (a posterior view of the part of the spine shown in FIG. 37). The front end 130 of the device is inserted into the disc space with the sides of the device dissecting the vertebrae as the implant advances. When the base member 195 contacts the side of the vertebrae as shown in FIGS. 39 and 40, and the side of the vertebrae obstructs further advancement of the implant, the implant is rotated (either clockwise or counter-clockwise) along the Z-axis using tools (not shown) thereby placing the top 110 and bottom 120 in contact with the endplates. In this second position, the implant can now be advanced further into the disc space and the base member 195 can fit inside without contacting the side of the vertebrae as shown in FIG. 41. The implant 100 is advanced further into the disc space to the desired position with the entire implant device 100 contained within the disc space.

The present invention also includes other embodiments, not shown, with a an internal screw that moves along a threaded path parallel to the longitudinal length of the device (along the Z-axis) with hinged sides (surfaces) enabling in situ expansion of the implant dimensions.

The present invention also includes embodiments where the right side 155 and the left side 165 of the extended member 190 are parallel to each other rather than the wedge shaped configuration shown in the figures.

One embodiment of the invention is a device with a right side or left side or both attached by hinges to the front end of the device. Another embodiment is a device with one or two anterior hinges and an additional hinge on the hinged right side and left side located at a distance posterior to the anterior hinge.

The present invention also includes embodiments with smooth and/or serrated surfaces.

The base member of the interbody device has two principal functions—to keep the extended member stable at its 90 degree rotated orientation and to increase surface area contact to prevent implant subsidence. The base member may be a separate implant (separate from an extended member) that is attached to the extended member part of the device outside or inside the disc space. The base member may be attached to the extended member by a hinge that is locked after graft insertion to a fixed angle. If the base member is separate, it may be attached to the exterior member with one or more screws during or after insertion. Both members of the device, either as one piece or two piece construction, may be made of the same biocompatible material, or the two members may be made from different materials that may differ in modulus of elasticity. Each member may also be made of a combination of different biocompatible materials.

The portions of the base member forming a part of the top and bottom of the implant which contacts the bony endplates may have a semi-circular, semi-elliptical, trapezoidal or rectangular shape.

If the base member is a separate implant that is secured to the extended member, it may also have a wedged shape similar to the extended member, but it will be locked to the extended member at a joining angle to ensure that the total construct will not rotate. The base member may have a central hollow intended to hold bone graft to enable interosseous fusion through the implant whether the base member is a separate implant or part of a singular implant with the extended member.

Another embodiment of the invention is an implant that can be expanded after its insertion into the interbody disc space by rotating a screw within the device thereby translating the screw anteriorly. Coupled to the screw's anterior movement (along the Z-axis) is a component that moves along the longitudinal axis (Z-axis) with tines that project in the transverse dimension. As the screw moves forward (anteriorly), the hinged right side and/or left side (now medially/laterally oriented after graft insertion and rotation) of the implant expand in the medial and/or lateral direction as the tines contact the hinged sides. Another embodiment of the invention is an implant with hinges on the sides and with a back (posterior) hinge that is attached to the component that moves when the internal screw is rotated. As the screw moves forward (anteriorly), the hinged right side and/or left side will expand in the medial and/or lateral direction with the apex of the expansion being at the middle hinge.

Embodiments of the invention including the internal screw and hinged or moveable side surfaces may or may not include a separable base member.

The invention also includes installation tools necessary to insert and rotate the intervertebral device or devices. The insertion tool attaches securely to the back (posterior aspect) of the implant or implants and may also interface with either the top and bottom or the sides of the implant at multiple sites or recesses. One embodiment of the invention is a hollow insertion device that accommodates an internal screw dowel that securely attaches to the back (posterior aspect) of the implant. Once the implant is inserted and rotated into place, the insertion screw dowel is removed and the screwdriver dowel required to turn the device's internal screw is inserted through the insertion device.

While the present invention has been illustrated by description of various embodiments and while those embodiments have been described in considerable detail, it is not the intention of applicant to restrict or in any way limit the scope of the appended claims to such details. Additional advantages and modifications will readily appear to those skilled in the art. The invention in its broader aspects is therefore not limited to the specific details and illustrative examples shown and described. Accordingly, departures may be made from such details without departing from the spirit or scope of applicants' invention.

We claim:

1. An interbody spinal implant comprising a front end, a back end, a top, a bottom, a left side, a right side, a height in said front end between said top and said bottom, a height in said back end between said top and said bottom, a thickness in said front end between said left side and said right side, a thickness in said back end between said left side and said right side, and a longitudinal length from the front end to the back end of said implant;
   said front end configured straight between said top and said bottom of said implant, said front end rounded between said left side and said right side of said implant;
   said thickness of said implant between said left side and said right side increasing from said front end towards said back end of said implant;
   said top and said bottom of said implant each curved in a generally convex shape between said front end and said back end of said implant, wherein a height of the front end of the implant is greater than a height of the back end of the implant;
   wherein said thickness in said front end is less than one half of said height in said front end;
   wherein said right side of said back end of said implant further comprises an outwardly curved bump out, wherein a maximum thickness of the implant at said bump out is at least twice the thickness of the front of said implant.

2. The implant according to claim 1, wherein said thickness in said front end is less than one third of said height in said front end.

3. The implant according to claim 1, wherein said thickness in said front end is less than one fourth of said height in said front end.

4. The implant according to claim 1, wherein said maximum thickness of the implant at said bump out is at least three times the thickness of the front of said implant.

5. The implant according to claim 1, wherein said left side of said implant is a generally flat surface.

6. The implant according to claim 5, wherein said right side of said implant is a generally flat surface.

7. The implant according to claim 6, wherein said surfaces on said left side and said right side of said implant from the front end to the bump out are at about a 6 degree angle to each other.

8. The implant according to claim 6, wherein said surfaces on said left side and said right side of said implant from the front end to the bump out are at about a 7 degree angle to each other.

9. The implant according to claim 1, wherein said left side of said implant is a convex curved surface.

10. The implant according to claim 1, wherein said right side of said implant from the front end to the bump out is a concave curved surface.

11. A angled interbody spinal implant comprising an extended member fixedly connected to a base member, said implant comprising, a front end, a back end, a top, a bottom, a left side, a right side, a height in said front end between said top and said bottom, a height in said back end between said top and said bottom, a thickness in said front end between said left side and said right side, a thickness in said back end between said left side and said right side, and a longitudinal length from the front end to the back end of said implant;
   said front end configured straight between said top and said bottom of said implant, said front end rounded between said left side and said right side of said implant;
   said thickness of said extended member between said left side and said right side increasing from said front end towards said base member in said back end of said implant;
   said top and said bottom of said implant each generally flat between said front end and said back end of said implant, wherein a height of the front end of the implant is greater than a height of the back end of the implant;
   wherein said thickness in said front end is less than one half of said height in said front end;
   wherein said thickness of said base member is at least twice the thickness of the front of said implant; and
   wherein a back surface of said base member forms is at an angle between 30 and 150 degrees with the left side of the extended member.

12. The implant according to claim 11, wherein said thickness in said front end is less than one third of said height in said front end.

13. The implant according to claim 11, wherein said thickness in said front end is less than one fourth of said height in said front end.

14. The implant according to claim 11, wherein said angle is approximately 90 degrees.

15. The implant according to claim 11, wherein the difference in height between said front end and said back end of said implant results in an angle between said surfaces on said top and said bottom between 15 to 25 degrees.

* * * * *